(12) United States Patent
Yang (10) Patent No.: US 10,639,325 B2
(45) Date of Patent: May 5, 2020

(54) POLYSACCHARIDE-POLYAMINE COPOLYMER AND USE THEREOF IN REDUCING URIC ACID CONCENTRATION IN PLASMA

(71) Applicant: Dazhi Yang, Beijing (CN)

(72) Inventor: Dazhi Yang, Beijing (CN)

( * ) Notice: Subject to any disclaimer, the term of this patent is extended or adjusted under 35 U.S.C. 154(b) by 60 days.

(21) Appl. No.: 15/559,196

(22) PCT Filed: Mar. 18, 2016

(86) PCT No.: PCT/CN2016/076715
§ 371 (c)(1),
(2) Date: Sep. 18, 2017

(87) PCT Pub. No.: WO2016/150341
PCT Pub. Date: Sep. 29, 2016

(65) Prior Publication Data
US 2018/0110801 A1  Apr. 26, 2018

Related U.S. Application Data (60) Provisional application No. 62/136,220, filed on Mar. 20, 2015.

(51) Int. Cl.
| | | |
|---|---|---|
| A61K 47/69 | (2017.01) | |
| C08G 73/02 | (2006.01) | |
| A61K 31/738 | (2006.01) | |
| A61K 31/785 | (2006.01) | |
| C08L 1/08 | (2006.01) | |
| C08L 3/20 | (2006.01) | |
| C08L 5/08 | (2006.01) | |
| B01J 20/26 | (2006.01) | |
| B01J 20/28 | (2006.01) | |
| B01J 20/30 | (2006.01) | |
| A61P 7/08 | (2006.01) | |
| C08B 15/06 | (2006.01) | |
| C08G 81/00 | (2006.01) | |
| C08G 83/00 | (2006.01) | |
| C08J 9/16 | (2006.01) | |

(Continued)

(52) U.S. Cl.
CPC .............. *A61K 31/785* (2013.01); *A61K 9/14* (2013.01); *A61K 31/738* (2013.01); *A61P 7/08* (2018.01); *B01J 20/264* (2013.01); *B01J 20/267* (2013.01); *B01J 20/28004* (2013.01); *B01J 20/28078* (2013.01); *B01J 20/28085* (2013.01); *B01J 20/3085* (2013.01); *C08B 15/06* (2013.01); *C08F 251/02* (2013.01); *C08G 73/0206* (2013.01); *C08G 81/00* (2013.01); *C08G 83/002* (2013.01); *C08J 9/16* (2013.01); *C08L 1/08* (2013.01); *C08L 3/20* (2013.01); *C08L 5/02* (2013.01); *C08L 5/08* (2013.01); *C08G 2101/00* (2013.01); *C08G 2210/00* (2013.01); *C08J 2205/022* (2013.01); *C08J 2207/10* (2013.01); *C08J 2387/00* (2013.01)

(58) Field of Classification Search
CPC ................ C09K 19/12; C09K 19/2007; C09K 19/2014; C09K 19/24; C09K 19/32; C09K 19/322; C09K 19/3469; C09K 19/3486; C09K 19/3491; C09K 19/3497; C09K 19/38; C09K 19/52; C09K 19/54; C09K 2019/0448; C09K 2019/122; C09K 2019/123; C09K 2019/2078; C09K 2019/525; C09K 2019/528; G02B 5/30; G02B 5/3016; G02F 1/13; G02F 1/1336
See application file for complete search history.

(56) References Cited

U.S. PATENT DOCUMENTS

| 4,663,163 A | 5/1987 | Hou et al. |
| 5,766,908 A | 6/1998 | Klein et al. |

(Continued)

FOREIGN PATENT DOCUMENTS

| CN | 101791408 A | 8/2010 |
| CN | 101864078 A | 10/2010 |

(Continued)

OTHER PUBLICATIONS

Kuga et al. (Journal of Chromatography A, 946 (2002) 283-289). (Year: 2002).*

(Continued)

*Primary Examiner* — Anna R Falkowitz
(74) *Attorney, Agent, or Firm* — Leason Ellis LLP (57) ABSTRACT

Disclosed is a pharmaceutical composition for treating hyperuricemia (HUA). The pharmaceutical composition includes a polysaccharide-polyamine copolymer and a pharmaceutically acceptable salt thereof as active ingredients. The polysaccharide-polyamine copolymer is formed by copolymerization of the following two parts: a selectively oxidized polysaccharide with 2,3-dialdehydo, and a polyamine with an amino functional group; the polyamine with an amino functional group and the selectively oxidized polysaccharide with 2,3-dialdehydo can form a net structure by means of covalent crosslinking, resulting in a hydrogel with an amino functional group or a granular polysaccharide-polyamine copolymer, wherein the amino functional group in the hydrogel with an amino functional group or the granular polysaccharide-polyamine copolymer can be protonated so as to form a cationic copolymer of a three-dimensional network structure having a protonated site, and the nitrogen content of the cationic copolymer and the nitrogen content of the polysaccharide-polyamine copolymer are above 12.3 wt %, and both the cationic copolymer and the polysaccharide-polyamine copolymer are water-insoluble.

20 Claims, 6 Drawing Sheets

(51) Int. Cl.
*A61K 9/14* (2006.01)
*C08F 251/02* (2006.01)
*C08L 5/02* (2006.01)
*C08G 101/00* (2006.01)

(56) References Cited

U.S. PATENT DOCUMENTS

| | | | |
|---|---|---|---|
| 2004/0010137 A1 | 1/2004 | Jaschinski et al. | |
| 2005/0002893 A1 | 1/2005 | Goldmann | |
| 2008/0317861 A1 | 12/2008 | Guan | |
| 2010/0272804 A1 | 10/2010 | Lu | |
| 2011/0142952 A1 | 6/2011 | Harris et al. | |
| 2012/0237470 A1 | 9/2012 | Dhal et al. | |
| 2014/0369952 A1 | 12/2014 | Liu et al. | |
| 2018/0056438 A1 | 3/2018 | Matsuyama et al. | |
| 2018/0071331 A1* | 3/2018 | Yang | A61K 31/738 |
| 2018/0099007 A1* | 4/2018 | Mitchell | A61K 31/738 |

FOREIGN PATENT DOCUMENTS

| | | |
|---|---|---|
| CN | 102154350 A | 8/2011 |
| CN | 102154351 A | 8/2011 |
| CN | 103030813 A | 4/2013 |
| CN | 103041403 A | 4/2013 |
| CN | 103113594 A | 5/2013 |
| WO | 0021572 A2 | 4/2000 |
| WO | WO 2014084790 A1 | 5/2014 |

OTHER PUBLICATIONS

Münster, Lukas, et al. "Stability and aging of solubilized dialdehyde cellulose." Cellulose 24.7 (2017): 2753-2766.
Kim, Ung-Jin, Masahisa Wada, and Shigenori Kuga. "Solubilization of dialdehyde cellulose by hot water." Carbohydrate polymers 56.1 (2004): 7-10.
Kim, Ung-Jin et al. "Polyallylamine-grafted cellulose gel as high-capacity anion-exchanger." Journal of Chromatography A 946.1-2 (2002): 283-289.
Office Action in corresponding CN Application No. 201610159108.4, dated Dec. 13, 2017 (an English translation attached hereto).
International Preliminary Report on Patentability in corresponding PCT Application No. PCT/CN2016/076715, dated Sep. 26, 2017.
International Search Report and Written Opinion in corresponding PCT Application No. PCT/CN2016/076715, dated Jun. 21, 2016.
International Search Report and Written Opinion in corresponding International Patent Application No. PCT/CN2016/076716, dated Jun. 20, 2016. 10 pages.
International Preliminary Report on Patentability in corresponding International Patent Application No. PCT/CN2016/076716, dated Sep. 26, 2017. 5 pages.
U.S. Appl. No. 15/560,311.

\* cited by examiner

POLYSACCHARIDE-POLYAMINE COPOLYMER AND USE THEREOF IN REDUCING URIC ACID CONCENTRATION IN PLASMA

CROSS-REFERENCE TO RELATED PATENT APPLICATIONS

This application is a U.S. National Phase Application under 35 U.S.C. § 371 of International Patent Application No. PCT/CN2016/07 6715, filed Mar. 18, 2016, and claims the benefit of priority under 35 U.S.C. Section 119(e) of U.S. Application Ser. No. 62/136,220, filed Mar. 20, 2015, all of which are incorporated by reference in their entireties. The International Application was published on Sep. 29, 2016 as International Publication No. WO 2016/150341 A1.

TECHNICAL FIELD

Embodiments of the present disclosure relate to amino-polysaccharide copolymers and use thereof in reducing uric acid concentration in plasma.

BACKGROUND

Hyperuricemia (HUA) is defined as: under normal purine diet, fasting serum uric acid level (twice, not on the same day) is higher than 420 μmol/L for male and 360 μmol/L for female.

According to statistic data, the incidence of asymptomatic hyperuricemia in the United States is 2%-13%; and in Europe is 2%-18%. The total number of gout patients in the United States in 2008 was 3.9% of the total population. In 2005, the incidence of gout in Britain and Germany is about 1.4% of the total population. With the continuous improvement of the quality of life in China, the prevalence of hyperuricemia (hyperuricemia, HUA) is increasing year by year. Especially in economically developed cities and coastal areas, the prevalence of HUA is 5%-23.5%. The domestic gout incidence rate was 1.14% in China (approximately 14, 000, 000) and increases by 0.97% every year. The number of patients with hyperuricemia is huge and increasing, and gout has become the second most metabolic disease in china.

SUMMARY

The present disclosure relates to a cross linked copolymer. More specifically, the present disclosure relates to amino-polysaccharide copolymer matrices and cationic polymer matrices. When protonated, the amino-polysaccharide copolymer can form a cationic copolymer matrix with a very high density cation site. In an embodiment of the present disclosure, the amino-polysaccharide copolymer has a three-dimensional structure, especially when hydrated.

In one aspect of the present disclosure, the amino-polysaccharide copolymer matrix is a reaction product of two preformed polymers or macromolecules. In one aspect of the present disclosure, the amino-polysaccharide copolymer can be considered as a two block copolymer. In one aspect of the present disclosure, the amino-polysaccharide copolymer is a reaction product of the following two parts: a selectively oxidized polysaccharide having a 2,3-dialdehyde moiety, and a amino polymer which provides an amino functionality. The reaction product comprises a hydrogel having an amino functionality or a particulate amino-polysaccharide copolymer, for example cellulose-amino polymer copolymer which has a tree-dimensional structure. When the amino group functionality of the amino-polysaccharide copolymer is protonated, the amine based functionalities provide cationic functionality for cationic polymers.

In one aspect of the present disclosure, primary amines, secondary amines and tertiary amines in the amino-polysaccharide copolymer can all be protonated. Among them, the primary amines are most easily protonated, followed by secondary amines and at last tertiary amines. Therefore, in the amino-polysaccharide copolymer, primary amines are mostly preferred, followed by secondary amines and at last tertiary amines. For example, in the amino-polysaccharide copolymer, a proportion of the primary amines to all the amine groups is at least 20%, or at least 40%, or at least 53%. Or, in the amino-polysaccharide copolymer, a proportion of a sum of the primary amines and secondary amines to all the amine groups is at least 30%, or at least 50%, or at least 70%.

In one aspect of the present disclosure, the polysaccharide is one or more selected from the group consisting of selectively oxidized cellulose, selectively oxidized starch, selectively oxidized chitosan, selectively oxidized dextran, selectively oxidized glycogen, and selectively oxidized chitin. "Selectively oxidized" refers to the oxidation of hydroxyl groups at the C2 and C3 positions, and an aldehyde group is formed along with the breaking of the C2-C3 bond. The oxidation process only produces aldehyde groups without producing carboxyl groups and does not break the polysaccharide chains.

In one aspect of the present disclosure, the polysaccharide is one or more selected from the group consisting of selectively oxidized cellulose and selectively oxidized chitosan. In the present disclosure, the so called "selectively oxidized cellulose", "selectively oxidized starch", "selectively oxidized amylopectin", "selectively oxidized chitosan", "selectively oxidized dextran", "selectively oxidized glycogen", and "selectively oxidized chitin", "selectively oxidized" means oxidize to dialdehyde. Selectively oxidized cellulose and selectively oxidized chitosan are important to the amino-polysaccharide copolymer as a medicine because they contain β-1,4-glycosidic bonds which can not be digested by humans. Polymers such as cellulose, starch, chitosan, dextran, glycogen, and chitin are oxidized to provide sufficient amount of 2, 3-dialdehyde to fully react with the amino polymer, and finally provide cross-linked matrices or three-dimensional structure having protonatable amine functionality.

The amino-polysaccharide copolymers matrices and cationic amino-polysaccharide copolymers matrices are not digestible by humans. The amino-polysaccharide copolymers matrices are three dimensional cross-linked matrices of polysaccharide polymers linked together with the amino polymers, especially when hydrated. In one aspect of the present disclosure, these three dimensional structure of cross-linked polymers are in a particulate form, the particulates having a size in the range of from about 100 μm to about 10 mm. The dehydrated form of the amino-polysaccharide copolymers or copolymeric matrices does not carry any permanent charges. These copolymers contain abundant amine groups and a small amount of imino groups. Amines and imines are classified as weak bases with pKa value in the range of from 9 to 11. When exposed to an aqueous environment with a pH lower than 9.0, the amino-polysaccharide copolymers or copolymeric matrices will be rehydrated, swelled, protonated and formed a cationic polymeric matrix.

The amino-polysaccharide copolymers particles and cationic polymeric particles have structures that are porous.

From one aspect, there are a large number of primary, secondary and tertiary substituted amines in the structure of the amino-polysaccharide copolymers. Both the gels and the polymeric particles comprise a homogeneous combination of the reaction product of the polysaccharide-derived polymers (with the aldehyde functionality) and amino polymers cross linkers as compared to a cellulosic shell encasing polymeric amino or amido compounds reacted with carboxylic acids. When in particulate form, the pores in the amino-polysaccharide copolymeric matrix and/or protonated amino-polysaccharide copolymeric matrix range in size of less than 50 μm. For example, size of the pores ranges from 100 nm to 50 μm, or from 200 nm to 40 μm, or from 300 nm to 30 μm, or from 400 nm to 20 μm, or from 500 nm to 10 μm, or from 800 nm to 5 μm. The amino-polysaccharide copolymer provided by embodiments of the present invention has larger pores, which is suitable for adsorbing negatively charged particles with larger volumes, such as nucleic acids. More specifically, because the pores are large, nucleic acids and other negatively charged particles with a large volume can be adsorbed into the pores, taking full advantage of the large surface area of the porous structure of the amino-polysaccharide copolymer. As described below, common drugs such as alkaline anion exchange resins, they do not have porous structure or a diameter of the pores is from a few nano-meters to ten nano-meters, are not conducive to the adsorption of large anionic macromolecules such as nucleic acids.

In one aspect of the present invention, the amino-polysaccharide copolymer structure provides amine substituents with a high density, such as primary amines, secondary amines, and quaternary amines. In one aspect of the present invention, hydrogel and particulate polymers can be provided by the compositions of the invention. The hydrogel and particulate polymers may contain a backbone chain, such as a cellulose chain, that is covalently cross-linked by a copolymer region of the amino polymer and has a three-dimensional dense interlocking network. The intricate three-dimensional mesh matrix formed by covalent cross-linking of cellulosic polymers and amino polymer crosslinker are contrasted with a cellulosic shell encasing polymeric amino of amido compounds reacted with carboxylic acids.

The polysaccharide polymers, such as cellulose, starch, chitosan, dextran, glycogen, and chitin, are oxidized in an amount effective to provide the 2,3-dialdehyde moiety which is reactive with the amino polymers to permit the oxidized polysaccharide polymers to react with amino polymers having amino functional groups which in turn provide the cross-linked structure having protonatable amino functionality of at least 12.5% weight percent, based upon the weight of the amino-polysaccharide copolymer. The amino polymers cross link the polysaccharide polymers, such as water soluble cellulosic polymers (having the di-aldehyde moieties) to provide the three dimensional structure of polysaccharide-derived "backbones" where multiple polysaccharide chains are linked with multiple chains of the amino polymers. These polysaccharide polymers are pre-existing polymers which are "blocks" or "backbones" linked together by pre-existing amino polymers which also are discrete amino blocks. In one form, the amino-polysaccharide polymers may be considered to be di-block copolymers. The linked backbones are bonded together as the covalent cross-linking products of the amino polymers (which form cross-linking blocks) and the selectively oxidized polysaccharide to provide cross-linked block copolymer and copolymeric matrices with high percent of amine content which may be protonated.

The latter amino-polysaccharide copolymers which form the particulate amino-polysaccharide copolymer structures may be protonated (in the human body, or by lowering the pH or by a reaction such as a hydride reduction of an amine after the cross-linking reaction) into cationic polymeric structures with extremely high charge densities. For example, the latter cross linked amino-polysaccharide copolymers which form the copolymeric matrices may be protonated, when exposed to an aqueous environment with a pH lower than 9.0. The amino-polysaccharide copolymer may be protonated in an amount effective to provide the cationic copolymeric matrices with an ammonium content of at least 12.5 wt % based upon the weight of the cationic copolymers. Further as previously noted, the resulting amino-polysaccharide copolymers are water insoluble. The existing water-soluble amino-polysaccharide copolymers before the present invention can form a stable, transparent and homogeneous colloidal solution in water, and the volume of the amino-polysaccharide copolymers is small and can be absorbed by cells. On the contrary, the amino-polysaccharide copolymer provided by embodiments of the present invention is formed through repeated covalent cross-linking between a plurality of oxidized polysaccharides containing aldehyde groups and a large number of amino polymers containing amine groups. As a result, the amino-polysaccharide copolymer provided by embodiments of the present invention has a large molecular weight and is easily precipitated in water. The volume of the copolymer is larger than 30 microns and can not be absorbed by cells.

The polysaccharide-amino polymer polymers provided by embodiments of the present invention have ammonium cations, which are positively charged or protonated substituted amines, e.g. $RNH_3^+$, $R_2NH_2^+$ and $R_3NH^+$ formed by the protonation of substituted amines, e.g. $RNH_2$, $R_2NH$ and $R_3N$. The amino polymer matrices are positively charged or protonated at the amine positions to form quaternary ammonium cations ($HNR3^+$), where one or more hydrogen atoms may be replaced by organic radical groups (indicated by R). The high charge density is effective to bind at least about 2.58±0.43 mmol/g under 6.25 mM phosphate condition at pH 7.0. In effect, the cationic matrices act as scavengers to remove phosphate from mammals including humans.

In one aspect of the present invention, the amino polymers are dendrimers which are macromolecular amines that have a core or center which includes amine groups and branches that include these functional groups which may be formed through a series of iterative reactions starting with the functional groups at the core or center to provide a highly branched amine polymer. In one aspect of the present invention, the dendrimer molecule may be round or substantially round or have a three dimensional morphology which is spherical or has an outer perimeter which is curvilinear or bounded by curved lines. In an important aspect of the present invention, the dendrimer has a nitrogen content of at least 24.5 wt %, or 25-80 wt % (based upon the weight of the dendrimer) which is effective to provide the amino-polysaccharide copolymer when protonated (which results in the cationic polymer matrix) with a protonated amine (ammonium ion) content of at least about 12.3 wt % (calculated on the basis of N atoms) based upon the weight of the cationic material. In another form, branched forms of the amino polymers may also be used alone or in combination with the dendrimeric forms.

The amino polymers include branched amino polymers, dendritic amino polymers, and the amino polymers generally described in U.S. Pat. No. 8,889,738 and WO2014/029888 which are incorporated as if fully rewritten herein.

Figure 3:
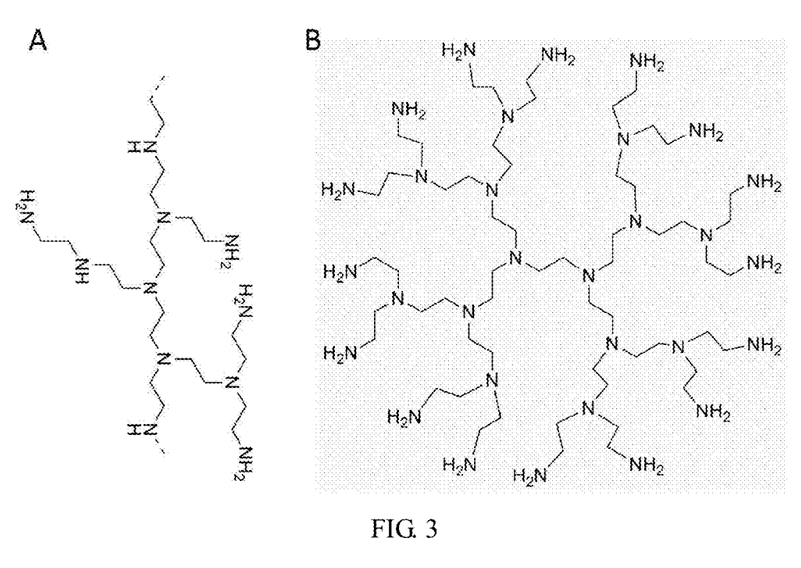
FIG. 3A is an example of branched polyethylenimine.
FIG. 3B is an example of dendritic polyethylenimine.

In an embodiment of the present invention, the amino polymers which provide the amino-polysaccharide copolymers with amino functionality (and cationic functionality when protonated after cross linking the polysaccharide polymers) are selected from the group consisting of polyethylenimine (PEI), polyallylamine, polypropylenimine and mixtures thereof. The polyethylenimine, polyallylamine, polyproplenime can be in their branched or dendrimeric form, such as found in the attached figures.

Methods for making the amino-polysaccharide copolymers and the cationic polymeric materials also are described herein. The method includes oxidizing polysaccharide polymers, then reacting the polysaccharide-derived polymers having 2,3 di-aldehyde moieties as described above with an amino polymer to provide the amino-polysaccharide copolymers. If a primary amine of the amino polymer is reacted with the cellulosic polymer and an imine is the reaction product, the imine can be converted to a substituted secondary amine by reducing the carbon nitrogen double bond to a single bond via a reduction reaction such as a hydride reduction reaction.

The oxidation level of polysaccharide, amine percent of the amino polymer, the size of the amino polymer, and the ratio of oxidized polysaccharide to the amino polymer all affect the formation of the amino-polysaccharide copolymer and copolymeric matrices. In one aspect of the present invention, the selective oxidized polysaccharide have oxidized glucose unit of at least 50 wt %, and preferably above 80 wt %. For poly(allylamine) (PLA), the molecular weight (Mw) is in the range of from about 17,000 Da to about 900,000 Da and the Mw for polyethyleneimine (PEI) is in the range of from about 25,000 Da to about 750,000 Da and preferably the Mn is in the range of from about 60,000 Da to about 750,000 Da. For PEI and/or PLA having Mw of 15,000 Da to 25,000 Da, the ratio of the polysaccharide polymer to the amino polymers is in the range of about 1:1 to about 1:3 by weight. When the Mw of the amino polymer is in the range of 65,000 Da to 750,000 Da, the ratio of polysaccharide polymer to amino polymer is in the range of about 1:5 to about 1:30 by weight.

A biocompatible cationic polymer is produced to sustain a high positive charge density resulting in strong bonding of polyvalent anions including phosphate, polynucleotides, negatively charged peptides, and anions of metals. etc.

In another aspect, the amino-polysaccharide polymers also may be used for removing or scavenging other anionic inorganic and/or organic solutes or particles, such as chloride, nitrite, bicarbonate, polynucleotides, polypeptides, bile acids, and oxalate containing compounds or ions. In one form, this may be performed for removal from the human body.

These and other aspects may be understood more readily from the following description and the appended drawings.

BRIEF DESCRIPTION OF THE DRAWINGS

In order to clearly illustrate the technical solution of the embodiments of the disclosure, the drawings of the embodiments will be briefly described in the following, it is obvious that the described drawings are only related to some embodiments of the disclosure and thus are not limitative of the disclosure.

FIG. 9 shows Reaction 1 representing the molecular structure of cellulose, which forms a backbone of the cellulose derivative polymer.

DETAILED DESCRIPTION

In order to make objects, technical details and advantages of the embodiments of the disclosure apparent, the technical solutions of the embodiment will be described in a clearly and fully understandable way in connection with the drawings related to the embodiments of the disclosure. It is obvious that the described embodiments are just a part but not all of the embodiments of the disclosure. Based on the described embodiments herein, those skilled in the art can obtain other embodiment(s), without any inventive work, which should be within the scope of the disclosure.

Unless otherwise defined, percentages in the present disclosure are mass (weight) percentages.

Generally, cross-linked copolymers are described herein and may be used for a variety of purposes, including, but not limited to removal of phosphate. The cross-linked copolymers generally include two components, namely, a backbone molecule and a functional polymer group cross-linked to the backbone molecule. In one approach, stable covalent bonds formed between a polysaccharide polymer and a large polymeric molecule provide a cross-linked copolymer that have cationic functionality when the amino and/or imine functionality in the polymeric material is protonated.

In one form, the cross-linked copolymer is an amino-polysaccharide copolymer. The amino-polysaccharide polymers, when protonated, can form cationic polymeric matrices having exceptionally high densities of cationic sites. In one form, the cross-linked copolymers provide a three dimensional structure, especially when hydrated. In some forms, the cross-linked copolymer can be even more specifically characterized as an amino-cellulosic copolymer that includes cellulose derived materials forming the polysaccharide component.

In one approach, a method of producing water insoluble cationic polymers as described herein includes an oxidation reaction and a nucleophilic carbonyl addition reaction. In one approach, the oxidation reaction may involve oxidation of a saccharide, by one approach, a polysaccharide such as microcrystalline cellulose, amylopectin, starch, chitosan, chitin, dextran, glycogen, or the like.

In one aspect, the polysaccharide polymers are selected from the group consisting of selectively oxidized cellulose, selectively oxidized starch, selectively oxidized chitosan, selectively oxidized dextran, selectively oxidized glycogen, selectively oxidized chitin, and mixtures thereof. Selectively oxidized refers to having the hydroxyls at the C2 and C3 positions from di-aldehyde oxidized with concomitant cleavage of the C2-C3 bond where the oxidation will not produce more carboxyl groups than aldehyde groups and will not cleavage the polysaccharide chain.

In one form, preferred polysaccharides suitable for synthesis into copolymers are insoluble polysaccharides made of alpha-D-glucose units or D-glucosamine, bound to each other through β-1,4 or β-1,6 glycosidic bonds, such as cellulose, amylose, chitosan, dextran, glycogen, and chitin. Through the oxidization reaction, abundant aldehyde groups are generated on these polysaccharides by selectively oxidizing the hydroxyl groups on C-2 and C-3 of glucose units. These newly added hydrophilic aldehyde groups significantly increase the water solubility of oxidized polysaccharides. Further, the polysaccharide polymers are selected from the group consisting of oxidized cellulose, oxidized starch, oxidized chitosan, oxidized dextran, oxidized glycogen, oxidized chitin and mixtures thereof. Cellulose and chitosan contain β-1, 4-glycosidic bond which cannot be digested by mammal. Starch, dextran and glycogen contain β-1, 6-glycosidic bond and are digestible by human. However, the amino-polysaccharide polymeric matrices described herein are not digestible, regarding of the starting polysaccharide material.

The cross-linked copolymers may be prepared in a variety of manners. In one form, the preparation takes place in three proceedings. First, through an oxidation reaction, abundant aldehyde groups are generated on polysaccharides by selectively oxidizing the hydroxyl groups on C2 and C3 of the glucose units. In one form, selective oxidation generally means to oxidize the hydroxyl groups in the C2 and C3 positions to the corresponding aldehydes with the concomitant cleavage of the C2-C3 bond. Such oxidization will not produce more carboxyl groups than aldehyde groups and will not cause cleavage of the polysaccharide chain. A carboxyl group cannot covalently cross-link amino polymers under the conditions of the oxidation reaction and that if formed carboxylic the carboxyl groups will undesirably form carboxylic acid in an aqueous environment. Further if formed, carboxylic acid will carry a negative charge which will undesirably interfere with the cationic charges formed when the amine groups are protonated.

Then, the aldehyde groups generated by selective oxidation of the polysaccharides react with primary amines of amino polymers to form imine derivatives, the intermediate amino-polysaccharide copolymers with unstable carbon-nitrogen double bonds. In one form, these are considered di-block copolymers. Next, a reduction reaction is carried out to convert the carbon-nitrogen double bonds of the imines into the carbon-nitrogen single bonds of amines in order to produce the stable amino-polysaccharide copolymers.

According to one form, the amino-polysaccharide polymeric matrices are the result of the reaction of two preexisting polymers or large molecules. In accordance with one form, the amino-polysaccharide polymers may be considered di-block copolymers. In one form, the amino-polysaccharide polymers are a reaction product of polysaccharide polymers having 2,3 di-aldehyde moieties and amino polymers having polyfunctional amino functionality reactive with the aldehyde moieties. The latter reaction product includes particulate cross linked copolymers which are the amino polysaccharide copolymers, such as amino cellulosic polymers, having a three dimensional structure. The amino functionality provides the cationic polymers with cationic functionality when the amino functionality in the amino-polysaccharide polymeric material is protonated.

It will be appreciated that the cross-linked copolymers as described herein may also be produced by methods other than oxidation of polysaccharides and glycoproteins.

An intermediate polymer resulting from the above-discussed oxidation reaction may have the following general formula:

Reaction 1, below, shows a schematic illustration of a method of obtaining an exemplary polymer from cellulose.

Cellulose is a naturally occurring polymer including glucose units interconnected by β-1, 4-glycosidic bonds. The molecular structure of cellulose, which forms a backbone of the cellulose derivative polymer is generally represented Reaction 1 as shown in FIG. 9.

As seen in Reaction 1 shown in FIG. 9, a polysaccharide such as microcrystalline cellulose may be oxidized to form an intermediate of cellulose. In one approach, carbonyl group-enriched intermediates such as aldehydes are generated by the oxidization of the polysaccharide backbone. In particular, reactive aldehyde groups may be created by the opening of the cellulose ring at multiple sites along the polysaccharide backbone. An exemplary cellulose oxidation reaction may be as follows:

A

In the above-illustrated chemical reaction, formula "A" generally represents cellulose, which may be any commercially available cellulose and formula "B" generally represents 2,3-dialdehyde that results from the oxidation of cellulose. As can be seen above, the 2, 3-dialdehyde cellulose illustrated above is a linear polymer with a structure similar to cellulose and includes one or more (and in the illustrated approach, two) reactive aldehyde groups. By one approach, cellulose may be pretreated with sulfuric acid to obtain sulfonic sites. In another approach, cellulose may be treated with hydrochloric acid.

While the exemplary chemical reaction above utilizes sodium periodate ($NaIO_4$) as an oxidizing agent, it will be appreciated that the oxidation of cellulose may be alternatively catalyzed by periodic acid, potassium periodate, or other cationic derivatives and salts of periodic acid, or the like. Other oxidizing agents include chlorine, hydrogen peroxide, peracetic acid, chlorine dioxide, nitrogen dioxide, persulfates, permanganate, dichromate-sulfuric acid, hypochlorous acid, hypohalites or periodates and a variety of metal catalysts. Oxidized polysaccharides including oxidized cellulose may contain carboxylic acid, aldehyde, and/or ketone groups, in addition to the original hydroxyl groups of the starting material, depending on the nature of the oxidant and reaction conditions.

Periodates are a unique form oxidants. Periodate-mediated oxidation of polysaccharides including cellulose is known to selectively oxidize the hydroxyl groups in the C2 and C3 positions to the corresponding aldehydes with the concomitant cleavage of the C2-C3 bond and is one of the most potent methods for polysaccharides modification. But other oxidants will produce more carboxyl groups than aldehyde groups and cause cleavage of chain of polysaccharides. The carboxyl group can not covalently cross-link amino polymer under the reaction condition as we described. Additionally, it will ionize and become carboxylic acid in aqueous solution. The carboxylic acid carries negative charges and disturbs the cationic function of our copolymers.

In one approach, the polymer intermediate formed as a result of the oxidation of polysaccharides as described above may then be subjected to nucleophilic carbonyl addition (e.g., hydride reduction) reactions with one or more branched cationic functional groups such as amino/imine polymers. Generally, polyfunctional primary amine-containing molecules can cross link with the aldehyde-containing oligosaccharide derived from polysaccharides such as cellulose and the like or glycoproteins and the like. By one approach, a large molecular weight polyfunctional primary amine agent may be used to provide for the formation of a high density of cationic sites on the derivative polysaccharide when later protonated. For most approaches, any polyamine (both the linear and branched) containing multiple primary amines can be used as a nucleophilic reagent.

The above-described reaction of a high molecular weight polyamine such as polyethylenimine with an aldehyde group-containing saccharide derivative results in formation of stable covalent bonds between the amino polymer and a polysaccharide derived backbone molecule. In one form, this provides cross-linked copolymer generally represented by formula "C" above and discussed in more detail below. In the above-illustrated exemplary reaction, the cellulose intermediate-containing reactive aldehyde groups formed as a result of the oxidation of cellulose with sodium periodate is subjected to a nucleophilic carbonyl addition reaction, and in this example, a hydride reduction reaction, with a cationic functional polymer such as with polyethylenimine to derive an exemplary insoluble cationic cellulose derivative polymer generally represented by formula "C".

While the above-illustrated exemplary reaction utilizes polyethylenimine as the nucleophilic agent, other exemplary polymers may be usable as nucleophiles in the reaction with the above-described intermediates of cellulose including reactive aldehyde groups. Some exemplary cationic functional polymers include, for example, poly(allylamine), poly(amidoamine), polypropylenimine tetramine and the like. Polyethylenimine, poly(allylamine) and polypropylenimine tetramine are synthetic polyamine containing polymers can be used in branched and/or dendrimer form.

In addition, branched or macrocyclic polyamines as described in International Publication No. WO 2014/029888, incorporated by reference herein in its entirety, may be suitable for the reactions as described herein. Furthermore, some exemplary linear polyamines suitable for the reactions described herein are listed below:

1,3-Diaminopropane (DAP)
Propane-1,3-diamine

After the above-described reaction of the polysaccharide derivative with a nucleophilic agent, the resulting product may be dried by evaporation or precipitation or other suitable technique. By one approach, amino-polysaccharide polymer material of uniform particle size may be achieved by screening the dried material through a suitable mesh. When in particulate form, the pores in the amino-polysaccharide copolymeric matrix and/or protonated amino-polysaccharide copolymeric matrix range in size of less than 50 µm, and in an important aspect from about hundreds of nanometer to about 50 micrometers.

By one approach, the amino density of the resulting cationic polymers is also controlled by the degree of polymerization, size of the nucleophile and the relative ratio of the polysaccharide substrate backbone and nucleophile. As used in this application, charge density refers to the number of primary, secondary and tertiary ammonium cations within the cationic polymer. More specifically, the charge carrier density refers to the number of charge carriers (e.g., electrons, ions) in a material (e.g., cationic polymers) per unit volume, not the actual charges on the carriers. According to one form, the amino-polysaccharide is prepared to provide the cross-linked structure having amino content (calculated by N atomic weight) of at least 12.5 weight percent, based upon the weight of the polysaccharide copolymer. In an important aspect, the dendrimer has an amino content (calculated by N atomic weight) of at least 24.5 wt %, preferably 25-80 wt % based upon the weight of the dendrimer which is effective to provide the amino-polysaccharide polymeric material when protonated (which results in the cationic polymer matrix) with a protonated content (calculated by N atomic weight) of at least about 12.3 wt %, based upon the weight of the cationic material.

The ranges may be qualitatively described as low, moderate, and high based on the molar ratios of the aldehyde-containing saccharide derivative and the functional primary amine nucleophile. In one approach, the aldehyde content and the primary amine content of the reactants are determined by quantitative titrimetry, while the $NH_2^+$ content of the final product is determined by Nuclear Magnetic Resonance Spectroscopy (NMR).

Figure 1:
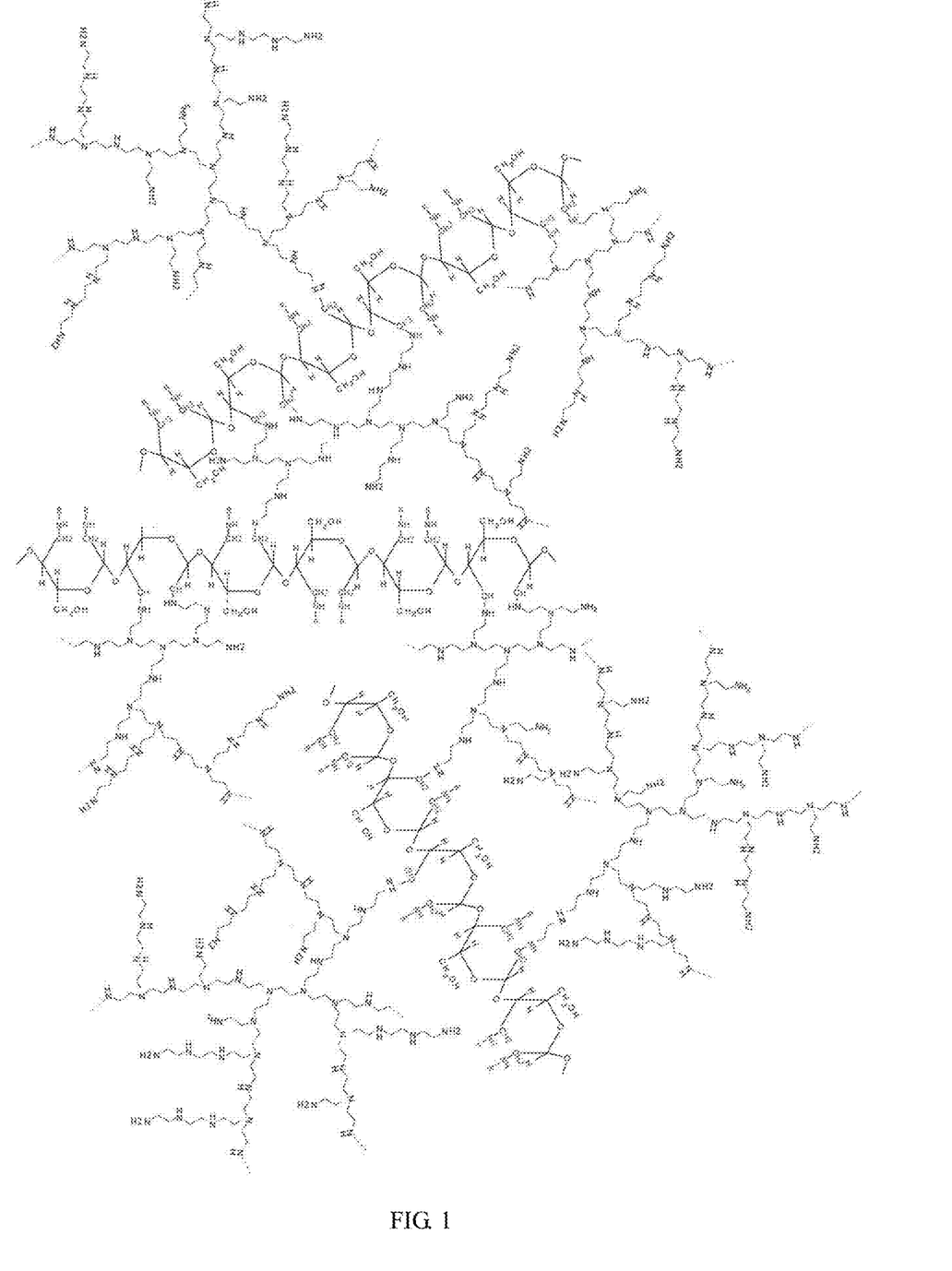
FIG. 1 is a general chemical structure for one exemplary form of a cross-linked copolymer, such as an amino-polysaccharide copolymer.
Figure 2:
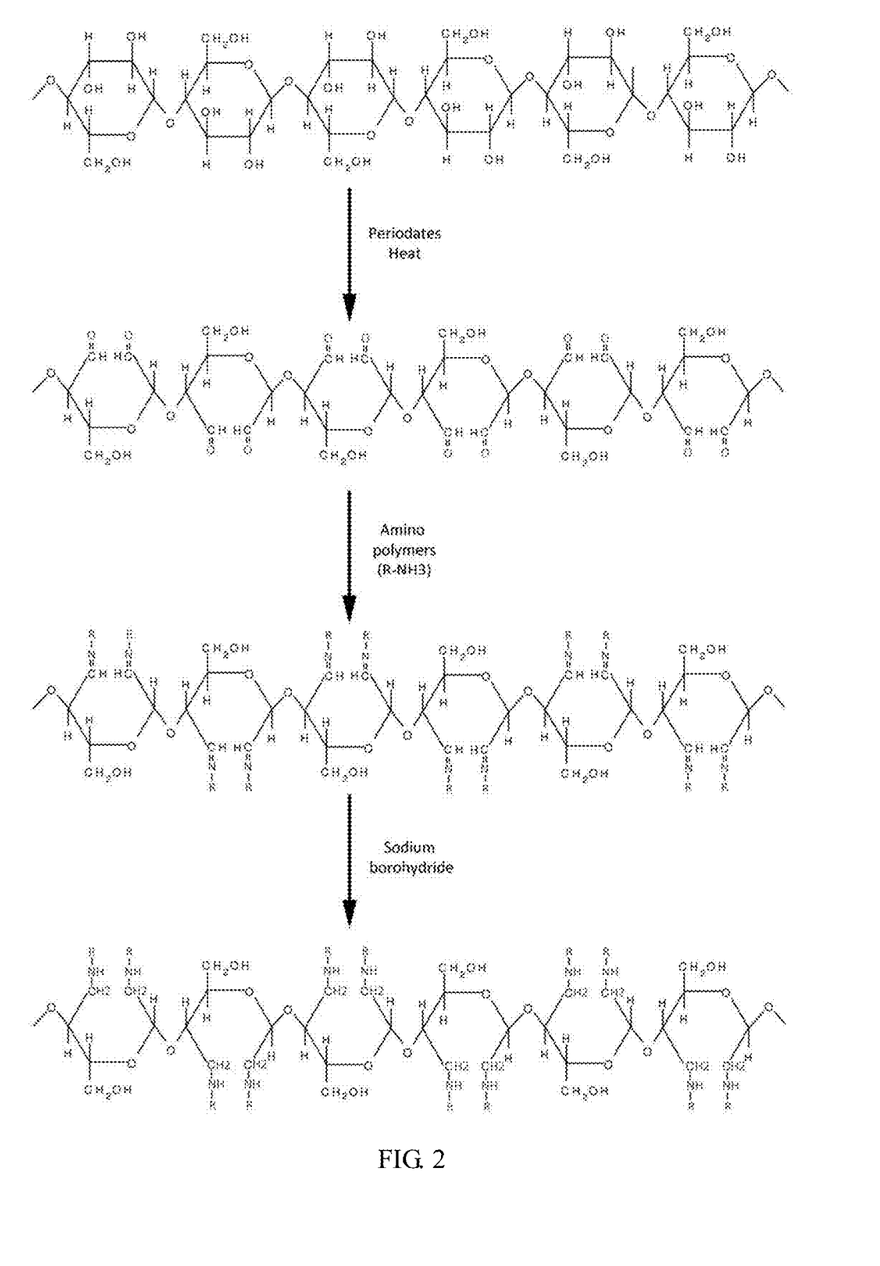
FIG. 2 is a schematic illustration of synthesis of exemplary cross-linked copolymers using a polysaccharide backbone.

Another exemplary process is provided in FIG. 2 illustrating the reaction of polysaccharides with amino materials.

The physical characteristics of the cross-linked copolymer resulting from the above-described oxidation and nucleophilic carbonyl addition reaction may be controlled by manipulating the conditions of the above-described reaction, for example, by varying the relative ratios of the substrate backbone and nucleophile, varying the types of functional groups used for reaction with the substrate backbone, and/or varying the time, pH, and/or temperature of the reaction. For example, increasing the temperature at which the reaction is run can lead to a corresponding increase in the size of the resulting water insoluble cationic polymer. In another example, increasing the reaction time can lead to a corresponding increase in the size of the resulting water insoluble cationic polymer. In yet another example, increasing the pH of the reaction conditions can lead to a corresponding increase in the size of the resulting cross-linked copolymer. In still yet another example, the size of the resulting cross-linked copolymer product can be controlled via selection of the molecular weight and ratios of the two major reactants, namely, the derivative polysaccharide (e.g., 2,3-dialdehyde cellulose) and the polyamine nucleophile (e.g., polyethylenimine).

In one approach, polyallylamine (PLA) with an average molecular weight of about 15,000 Da to about 900,000 Da or polyethylimine (PEI) with an average molecular weight of about 25,000 Da to about 750,000 Da can be used. For example, PLA with an average molecular weight of approximately 15,000 Da, 17,000 Da, 65,000 Da, or 900,000 Da, or PEI with an average molecular weight of approximately 25,000 Da or 750,000 Da obtained from Sigma-Aldrich may be used. The ratio of the polysaccharide backbone component (e.g., cellulose) to the cationic site forming functional polymer (e.g., polyethylenimine) used in the reaction may depend upon the molecular weight of the cationic site forming functional polymer. For example, for PEI and PLA with molecular weight from about 15,000 Da to about 25,000 Da, the weight ratio of the derivative cellulose to polyamine may range from about 1:1 to about 1:8. In one approach, when PEI and PLA with molecular weight ranging from about 65,000 to about 750,000 is used, the weight ratio of the derivative cellulose to polyamine ranges from about 1:5 to about 1:20.

In one aspect the amino polymers are dendrimers which are macromolecular amines that have a core or center which includes amine groups and branches that include these functional groups which may be formed through a series of iterative reactions starting with the functional groups at the core or center to provide a highly branched amine polymer. In one aspect, the dendrimer molecule may be round or substantially round or have a three dimensional morphology which is spherical or has an outer perimeter which is curvilinear or bounded by curved lines. In an important aspect the dendrimer has an amino content (calculated by N atomic weight) of at least about 24.5 wt %, and preferably in the range of 25-80 wt %, based upon the weight of the dendrimer, which is effective to provide the amino-polysaccharide polymeric material when protonated (which results in the cationic polymer matrix) with a protonated content of at least about 12.3 wt % (calculated by N atomic weight) based upon the weight of the cationic material.

The particle size of the cross-linked copolymer product may be regulated by coupling the crosslinking polyfunctional primary amines (e.g., polyethylenimine) with polysaccharide derivatives (2, 3-dialdehyde cellulose) having low, intermediate, and very high molecular weights (e.g., ranging from about 15,000 Da to 750,000 Da) to obtain nanoparticles, microparticles, and millimeter sized particles.

The amino-polysaccharide polymeric matrices are three dimensional cross linked matrices of polysaccharide polymers linked together with the polyamino polymers, especially when hydrated. These three dimensional structure of cross-linked polymers are in a particulate form, the particulates having a size in the range of from about 100 μm to about 10 mm. The dehydrated form of the amino-polysaccharide copolymers or copolymeric matrices does not carry any permanent charges. These copolymers contain abundant amine groups and a small amount of imino groups. Amines and imine are classified as weak bases with pKa value in the range of from 9 to 11. When exposed to an aqueous environment with a pH lower than 9.0, the amino-polysaccharide copolymers or copolymeric matrices will be rehydrated, swelled, protonated and formed a cationic polymeric matrix.

The polysaccharide polymers, such as cellulose, starch, chitosan, dextran, glycogen, and chitin, are oxidized in an amount effective to provide the 2, 3-dialdehyde moiety which is reactive with the amino polymers to permit the oxidized polymers to react with polyamino functional polymers which in turn provide the cross-linked structure having amino functionality (calculated by N atomic weight) of at least 12.5 weight percent, based upon the weight of the polysaccharide copolymer. The amino polymers cross link the polysaccharide polymers, such as water soluble cellulosic polymers (having the di-aldehyde moieties) to provide the three dimensional structure of polysaccharide-derived "backbones" where multiple polysaccharide chains are linked with multiple chains of the amino polymers. These polysaccharide polymers are pre-existing polymers which are "blocks" or "backbones" linked together by pre-existing amino polymers which also are discrete amino blocks. In one form, the amino-polysaccharide polymers may be considered to be di-block copolymers. The linked backbones are bonded together as the covalent cross-linking products of the amino polymers (which form cross-linking blocks) and the selectively oxidized polysaccharide to provide cross-linked block copolymer and copolymeric matrices with high percent of amine content which may be protonated.

The resulting cross-linked copolymer, such as an amino-polysaccharide copolymer, may be prepared in the form of a solid powder, a gel, and the like. Further, the cross-linked copolymer may have a phosphate binding capacity of 2.59±0.43 mmol/g, when the phosphate level is 6.25 mM at pH 7 in vitro. In one form, at pH 6, the cross-linked copolymer has the maximum phosphate binding capacity of 2.56±0.27 mmol/g, when the phosphate concentration is 5 mM, the physiological phosphate level, in vitro. According to one form, the cross-linked copolymer may show a stable phosphate binding property after storage in water at room temperature for at least 3 months. According to one form, the swallow factor of the cross-linked copolymer may be less than about 6.43±0.36 fold.

Uric acid is the ultimate metabolite of purine, and purine is the metabolic product of nucleic acid during oxidation. Therefore, purine in human body comes mainly from dietary intake of nucleic acids containing food and the aging cells of human body producing nucleic acids during metabolism. Of these nucleic acids, 50% of ribonucleic acid (RNA) and 25% deoxyribonucleic acid (DNA) are oxidized to purines in the body firstly. These purines are eventually oxidized to uric acid (2,6,8-trioxypurine) in the liver. Wherein, ⅔ uric acid is excreted in urine through the kidneys, and ⅓ uric acid is excreted through feces and sweat. A large intake of foods rich in purines and nucleic acids, a large number of cells die in the body, and endogenous purine metabolic disorder will all result in producing too much uric acid in the body. When the concentration of uric acid in the blood is greater than 7 mg/ml, hyperuricemia, the acidity of the body fluid increases, affecting the normal function of human cells. Symptoms do not happen in many hyperuricemia patients in a lifetime. This is called asymptomatic hyperuricemia.

While hyperuricemia is highly popular, a wealth of research evidence highlights the dangers of hyperuricemia. If patients are not treated for a long time, under certain inducement, supersaturated uric acid will form acicular crystals and deposit in synovial fluid. These crystals are regarded as invaders by white blood cells and are swallowed by white blood cells. After being swallowed, inflammatory factors are released to cause acute gout. In addition to causing acute gouty arthritis, gout, chronic arthritis, gouty nephropathy, acute renal failure and urinary calculi, HUA is closely related to metabolic syndrome, type II diabetes, hypertension, cardiovascular disease, chronic kidney disease, and gout etc., and is independent risk factor in the occurrence and development of the above described diseases.

The existing drugs for treating hyperuricemia are mainly drugs for inhibiting the production of uric acid and drugs for increasing uric acid excretion. Among the existing drugs, xanthine oxidase inhibitor allopurinol is the most important one. However, xanthine oxidase inhibitor allopurinol has high toxicity and causes many adverse reactions including gastrointestinal symptoms, skin rashes, liver function impairment and myelosuppression. This drug even causes allopurinol hypersensitivity syndrome (Chinese Han people are more risky in hypersensitivity). A drug of same type, "Febuxostat" also causes myocardial necrosis, liver damage, limb weakness, numbness, shortness of breath and hypersensitivity. Benzbromarone and probenecid can inhibit the active reabsorption of urate in the renal tubules and increases the excretion of urate, thereby reducing the concentration of urate in the blood. But urinary tract stones are easily formed when taking these medicines. Thus it is necessary to drink plenty of water, and the amount of water should not be less than 1500-2000 mL per day, when these medicines are administrated. At the same time, such drugs have serious hepatotoxicity and can cause liver damage.

Uricase can catalyzes the oxidation of uric acid to more soluble allantoin, thereby lowering plasma uric acid levels. However, this drug is used through intravenous injection, which takes 30 minutes every day. Thus application of uricase is extremely inconvenient and increase chance of developing infusion reaction.

A large number of clinical studies have shown that alkaline anion exchange resin "Sevelamer" can significantly reduce plasma uric acid content. In vitro binding experiments showed that 1 gram "Sevelamer" can bind 0.28 grams of urate. Therefore, the reduction of uric acid by "Sevelamer" may be due to its binding and inhibition of urate absorption in the food and intestinal tract.

The amino-polysaccharide copolymer provided by embodiments of the present invention can significantly reduce the uric acid level in plasma of experimental animals. Nucleic acids in food and digestive tract necrosis cells are mostly conjugated to proteins to form nucleoproteins. The nucleoproteins are degraded into nucleic acids and proteins under the action of gastric acid in the stomach or protease in the small intestine. Nucleic acids (DNA and RNA) in the small intestine are digested by deoxyribonuclease (DNase) and ribonuclease (RNase) into oligonucleotides (small polynucleotides) and some single nucleotide, respectively. The small intestine mucous membrane secretes diesterase and nucleotide enzyme, these enzymes have certain specificity to the substrate. Oligonucleotides are hydrolyzed into single nucleotides by diesterases. The protonated amino-polysaccharide copolymers provided by embodiments of the present invention bind to nucleic acids, polynucleotides, oligonucleotides, and purine nucleotides in intestinal tract through anion-cation interaction with phosphate group of nucleotides. Through the above interaction, nucleic acids, polynucleotides, oligonucleotides, and purine nucleotides are restricted from being degraded into nucleosides by the digestive enzymes and finally being absorbed by the small intestine. Thus reducing the amount of purine absorbed by the small intestine is reduced, thereby reducing the plasma uric acid content. Amino-polysaccharide copolymers are also alkaline anion exchange resins. Therefore, the amino-polysaccharide copolymer provided by embodiments of the present invention can also block the absorption of urate produced by food in small intestinal, thereby reducing the plasma uric acid concentration.

The inventor of the present invention finds that, the amino-polysaccharide copolymer provided by the embodiments of the present invention can be used as a prototype drug for treatment of hyperuricemia. The amino-polysaccharide copolymers provided by the embodiments of the present invention contain abundant amine groups and a small amount of imino groups, when exposed to an aqueous environment with a pH lower than 9.0, the amino-polysaccharide copolymers or copolymeric matrices will be rehydrated, swelled, protonated, and at last form a cationic copolymeric matrix. The cationic copolymer matrix has a high density of positive charges and can bind to phosphate group of ribonucleic acid or deoxyribonucleic acid, and thus interfere with both digestion of polynucleotides, oligonucleotides and purine nucleotides and absorption of purine nucleosides in the small intestines, and finally blocking absorption of urate in the food and produced in the intestines, thereby reducing plasma uric acid concentration. At the same time, compared with the conventional alkaline anion exchange resins, the amino-polysaccharide copolymer provided by the embodiments of the invention has various advantages. First, the amino-polysaccharide copolymer provided by embodiments of the present invention is hardly absorbed by the gastrointestinal tract and therefore does not disturb normal physiological activity in the body; second, the amino-polysaccharide copolymer provided by embodiments of the present invention has large pore size and is more suitable for adsorbing negatively charged macromolecules; third, the manufacturing cost of the amino-polysaccharide copolymer provided by embodiments of the present invention is very low.

The therapeutic potential of the amino-polysaccharide copolymer provided by embodiments of the present invention for treating hyperuricemia can be indicated by following experimental results. 1 gram of amino-polysaccharide copolymer (1:20 DAC:PEI750K) can bind 5-6 mmol phosphate in vitro. 1 gram of amino-polysaccharide copolymer (1:20 DAC:PEI750K) can bind 6.0-8.0 grams of DNA/RNA in vitro. The amino-polysaccharide copolymers bind with nucleic acids, polynucleotides, oligonucleotides, and purine nucleotides in gastrointestinal tract through interacting with phosphate group of ribonucleic acid or deoxyribonucleic acid. Through binding and trapping, the amino-polysaccharide copolymers impede both digestion and absorption nucleic acids, polynucleotides, oligonucleotides, and purine nucleotides in gastrointestinal tract, eventually, reduce concentration of plasma uric acid.

The structure, composition and preparation method of the amino-polysaccharide copolymer of the present disclosure are described more specifically through examples. The characterization of the amino-polysaccharide copolymer adopts common methods in this field. For example, the nitrogen contents of amino polymers and amino-polysaccharide copolymers can be calculated by molecular formula or measured by elemental analysis. The pore sizes of the amino-polysaccharide copolymers were measured by optical microscopy. FI-IR is performed by a Thermo Nicolet 4700 FT-IR Spectrometer.

Example 1 Synthesis of Amino-Polysaccharide Copolymers 1. 2,3-dialdehyde cellulose (DAC) was synthesized by sodium periodate oxidation 1.1. Soluble 2,3-dialdehyde cellulose (DAC) is prepared by oxidizing cellulose with sodium periodate (oxidized glucose units >80%)

1) Disperse 10 grams of cellulose (particle size <100 nm, or <20 micrometers or <50 micrometers; or fibers) with 200 milliliters of deionized water;
2) Add 20 grams of sodium periodate;
3) Adjust pH to 3 with 6× HCl;
4) Degassing and purging with nitrogen gas;
5) Stir for 4 hours in darkness, at 60° C. at pH 3;
6) Terminate the reaction by adding 10 ml of ethylene glycol;
7) Dialysis products for 3 days with deionized water;
8) Centrifugation was performed at 40000 g for 30 min to collect soluble DAC as supernatant and to remove insoluble DAC;
9) The collected supernatant was freeze-dried (optional).

1.2. insoluble 2,3-dialdehyde cellulose (DAC) is prepared by oxidizing cellulose with sodium periodate (oxidized glucose units <80%)

1) Disperse 10 grams of cellulose (particle size <100 nm, or <20 micrometers or <50 micrometers; or fibers) with 200 milliliters of deionized water;
2) Add 10 grams of sodium periodate;
3) Adjust pH to 3 with 6× HCl;
4) Degassing and purging with nitrogen gas;

5) Stir for 4 hours in darkness, at 60° C. and at pH 3;
6) Terminate the reaction by adding 10 ml of ethylene glycol;
7) Wash products with deionized water;
8) Centrifugation was performed at 2,000 g for 10 min to collect insoluble DAC;
9) The insoluble DAC after washing was re-dispersed with deionized water (DI, water);
10) The collected insoluble DAC was freeze-dried (optional).

PLA: poly(allylamine); PEI: polyethyleneimine

| Type of branched PEI or PLA | weight ratio of DAC to PEI/PLA that hydrogel state amino-polysaccharide copolymer can be achieved |
| --- | --- |
| PEI Mw. 25K | From 1:1 to 1:3 |
| PEI Mw.750K | From 1:10 to 1:30 |
| PLA Mw.15K | From 1:1 to 1:5 |
| PLA Mw.58K | From 1:5 to 1:20 |

2. Preparation of Amino-Polysaccharide Copolymer from Soluble DAC and PEI

The molecular weight (Mw) of PEI is 750K, and the weight ratio of DAC to PEI is 1:10.

1) Add 45 grams of branched polyethylenimine (PEI) (molecular weight 750K, 50 wt. % aqueous solution) to a 500 mL beaker;
2) Adjust pH of PEI solution to 1 by adding 37% HCl;
3) 5 grams of the branched polyethylenimine (PEI) (molecular weight 750K, 50 wt. % aqueous solution) were added to a 50 ml centrifuge tube and diluted with an equal volume of deionized water;
4) The pH of the 100 ml solution containing 5 grams of soluble DAC is adjusted to 1 by adding 6× HCl;
5) PEI solution and DAC solution were incubated on ice for 10 minutes;
6) Mix a solution containing 45 grams of PEI with a solution containing 5 grams of DAC, and incubate on ice for 10 minutes, stirring at the same time;
7) The solution containing 5 grams of diluted PEI is rapidly added to the PEI-DAC mixture, incubated on ice and stirred for 5 minutes at 1000 rpm;
8) Keep the mixture on the ice without stirring until the gel is fully formed;
9) The hydrogel is incubated at 70° C. for 60 minutes;
10) The water gel is separated by mesh sieve to obtain uniform size of gel particles;
11) Add deionized water to adjust the total volume of hydrogel particles suspension up to 1000 ml;
12) The suspension of hydrogel particles was incubated for 60 minutes at 70° C., and the pH value of the suspension was detected every 10 minutes, and adjusted to 8.5 by adding 5M sodium hydroxide solution;
13) The gel particles precipitate at room temperature by gravity;
14) After the supernatant was aspirated, the granules were incubated for 60 minutes in 4 L, 100 mM sodium bicarbonate solution at pH 8.5 under stirring, and were precipitated at room temperature by gravity;
15) After the supernatant was removed, the precipitated gel particles were washed two times with 4 liters of deionized water and precipitated by gravity;
16) After the supernatant was aspirated, the gel particles were reduced by adding 10 g of sodium borohydride and incubated at room temperature for 72 hours;
17) The reduced gel particles were washed with deionized water to remove excess sodium borohydride and PEI until the pH of the solution was between 5 and 6;
18) Freeze-dried the gel particles after washing (optional). The final product is white or light yellow hydrogel particles, the yield is 70-80%, nitrogen content is about 20%.

Example 2 Synthesis of Amino-Polysaccharide Copolymers

The reaction conditions are the same as those of Example 1. The difference is that the molecular weight of PEI is 750 K, DAC to PEI weight ratio is 1:20. The final product is white or light yellow hydrogel particles, the yield is 50-60%, nitrogen content is about 21.5%.

Example 3 Synthesis of Amino-Polysaccharide Copolymers

The reaction conditions are the same as those of Example 1. The difference is that DAC to PEI weight ratio is 1:30. The final product is white or light yellow hydrogel particles, the yield is 20-40%, nitrogen content is about 22%.

Example 4 Synthesis of Amino-Polysaccharide Copolymers

The reaction conditions are the same as those of Example 1. The difference is that the molecular weight of PEI is 25 K, DAC to PEI weight ratio is 1:1. The final product is white or light yellow solid particles, the yield is 60-70%, nitrogen content is about 12.5%.

Example 5 Synthesis of Amino-Polysaccharide Copolymers

The reaction conditions are the same as those of Example 1. The difference is that the molecular weight of PEI is 25 K, DAC to PEI weight ratio is 1:2. The final product is white or light yellow solid particles, the yield is 20-40%, nitrogen content is about 15%.

Example 6 Synthesis of Amino-Polysaccharide Copolymers

The reaction conditions are the same as those of Example 3. The difference is that DAC to PEI weight ratio is 1:3. The final product is white or light yellow hydrogel particles, the yield is 10-20%, nitrogen content is about 16.9%.

Example 7 Synthesis of Amino-Polysaccharide Copolymers

Preparation of Granular Amino-Polysaccharide Copolymers from Insoluble DAC and Polyamines.

1) 50 g poly(allylamine hydrochloride) (molecular weight 58K and 15K) or polyethyleneimine (molecular weight 750K and 25K) are dispersed in deionized water to achieve a total volume of 100 mL;
2) Adjust the pH of the solution to 9 with 37% HCl or NaOH and adjust the total volume to 300 mL by adding deionized water;
3) Disperse 50 g the insoluble DAC with 100 mL deionized water;
4) After adjusting pH to 2 with 6N HCl, the insoluble DAC suspension was stirred at 500 rpm and added to the polyamine solution at 10 ml/min speed, and then incubated at 70° C. for 60 minutes;

5) Hydrogel is separated by mesh sieve to achieve uniform size of gel particles;
6) Titrate the suspension with 5M sodium hydroxide solution to pH 8.5;
7) Adding deionized water to adjust the total volume of the hydrogel particles suspension to 500 mL and pH to 8.5;
8) The suspension of the hydrogel particles was incubated at 70° C. for another 60 minutes, and the suspension pH was detected every 10 minutes, and adjusted to pH 8.5 by adding 5M sodium hydroxide solution;
9) The hydrogel particles are precipitated at room temperature by gravity;
10) After the supernatant was removed, the granules were incubated for 60 minutes in 4 L, 100 mM sodium bicarbonate solution at pH 8.5 under stirring, and were precipitated at room temperature by gravity;
11) After the supernatant was removed, the precipitated gel particles were washed twice with 4 liters of deionized water and precipitated by gravity;
12) The gel particles were reduced by adding 10 g of sodium borohydride and incubated at room temperature for 72 hours;
13) The reduced gel particles were washed with deionized water to remove excess sodium borohydride and polyamine until the pH of the solution was between 5 and 6;
14) Freeze drying the washed gel particles (optional), the final product is white or light yellow solid particles, the yield is 50-80%, nitrogen content is about 12.5%.

Example 8 Synthesis of Amino-Polysaccharide Copolymers

The reaction conditions are the same as those of Example 7. The difference is that polyamine is PLA (MW, 58K), and the weight ratio of DAC to PLA is 1:5. The obtained final product is white or light yellow solid particles, the yield is 50-80%, nitrogen content is about 18%.

Example 9 Synthesis of Amino-Polysaccharide Copolymers

The reaction conditions are the same as those of Example 8. The difference is that the weight ratio of DAC to PLA is 1:10. The obtained final product is white or light yellow hydrogel particles, the yield is 40-60%, nitrogen content is about 20%.

Example 10 Synthesis of Amino-Polysaccharide Copolymers

The reaction conditions are the same as those of Example 8. The difference is that the weight ratio of DAC to PLA is 1:20. The obtained final product is white or light yellow hydrogel particles, the yield is 30-50%, nitrogen content is about 21%.

Example 11 Synthesis of Amino-Polysaccharide Copolymers

The reaction conditions are the same as those of Example 8. The difference is that the weight ratio of DAC to PLA is 1:2. The obtained final product is white or light yellow hydrogel particles, the yield is 25-45%, nitrogen content is about 12.8%.

Example 12 Synthesis of Amino-Polysaccharide Copolymers

The reaction conditions are the same as those of Example 8. The difference is that the weight ratio of DAC to PLA is 1:3. The obtained final product is white or light yellow hydrogel particles, the yield is 30-55%, nitrogen content is about 13%.

Example 13 Morphology of Amino-Polysaccharide Copolymers

Figure 4:
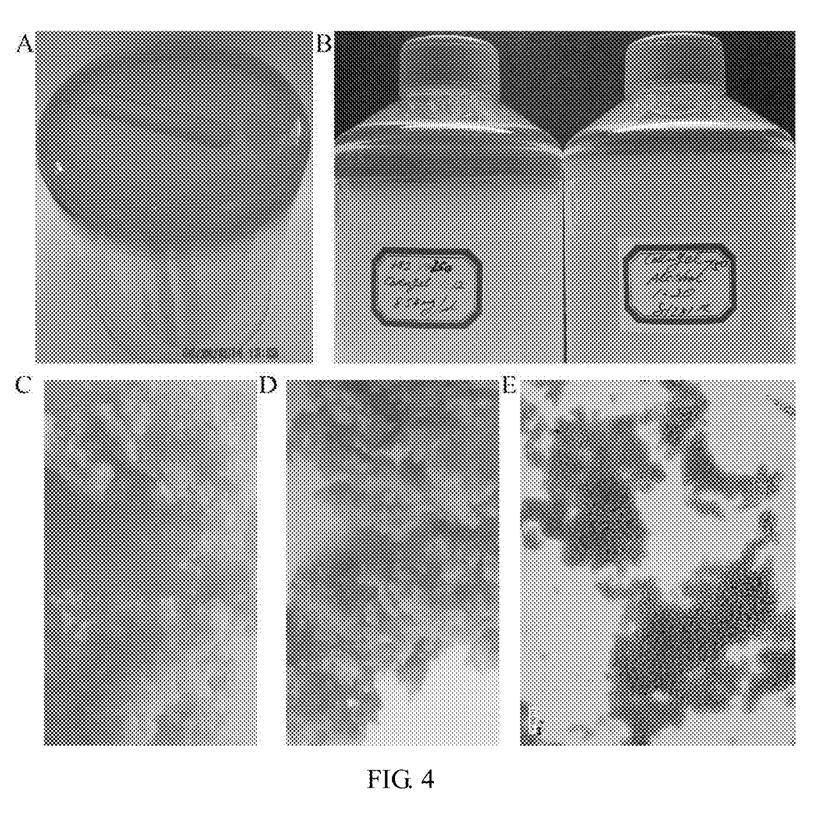
FIG. 4 is a surface topography of a product provided by some embodiments of the present invention.

FIG. 4 shows the morphology of the products obtained by embodiments of the present invention. FIG. 4A shows a cationic copolymer "CelloPhos" formed after the protonation of an amino-polysaccharide copolymer; FIG. 4B shows a granular "CelloPhos" after reduction; FIG. 4C shows a particulate "CelloPhos" (DAC:PEI 750K=1:20) obtained after drying of the final product (which is obtained in accordance with the proceedings of Example 1) in air; FIG. 4D shows a particulate "CelloPhos" (DAC:PEI 750K=1:20) obtained after drying of the final product (which is obtained in accordance with the proceedings of Example 2) in air; FIG. 4E is a phase contrast map of granular "CelloPhos" stained with eosin. The conclusions that can be drawn from the results are:

1) The amino-polysaccharide copolymer obtained by embodiments of the present invention is a hydrophilic material hydrogel obtained under special copolymerization conditions;

Homogeneous and small size hydrogels were obtained by sieving;

Yellow powder particles can be obtained by drying in the air;

Protonated amino-polysaccharide copolymer particles can bind with negatively charged dye eosin;

The amino-polysaccharide copolymer particles have porous and multilayered structure, which enhances their adsorption and binding ability to phosphate.

Example 14 FT-IR Spectra of Amino-Polysaccharide Copolymers

Figure 5:
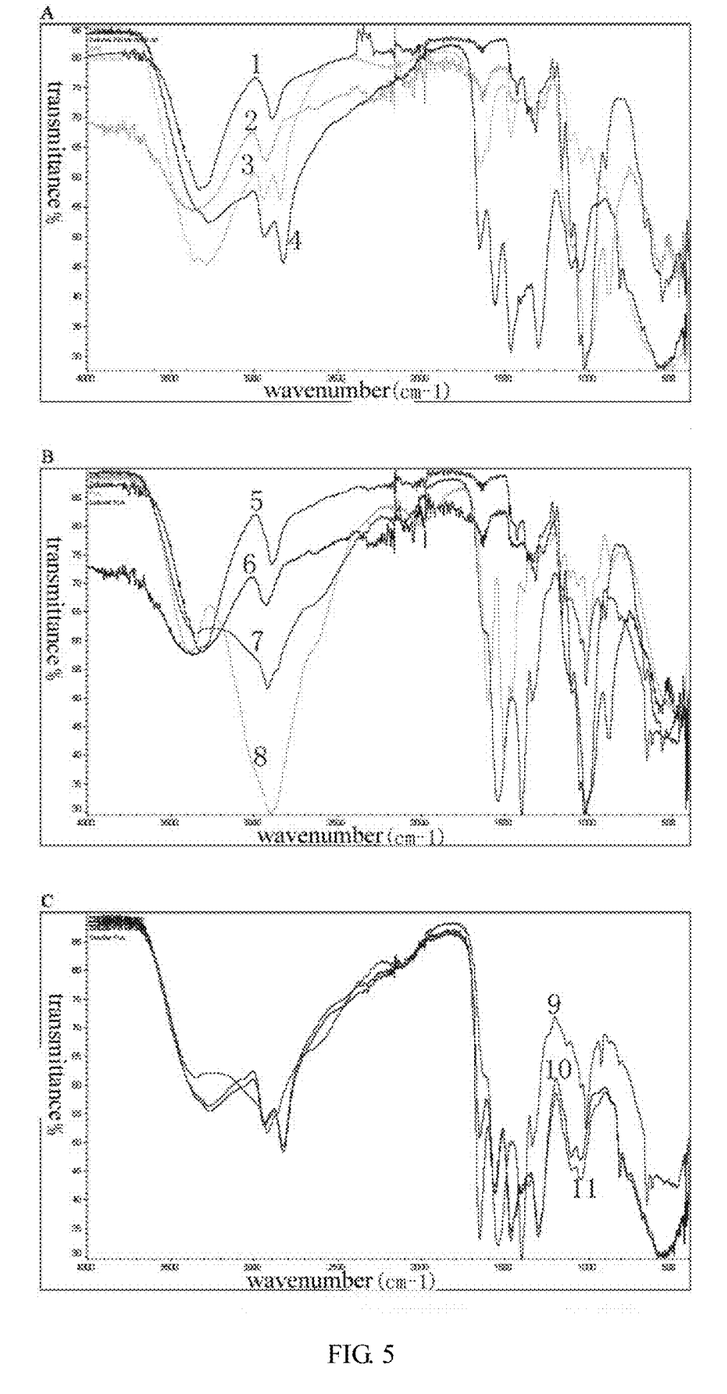
FIG. 5 is FT-IR infrared spectra of reactants and products in some embodiments of the present invention.

FIG. 5 shows FT-IR spectra of amino-polysaccharide copolymers obtained by embodiments of the present invention. Wherein, FIG. 5A, 1: cellulose; 2: selectively oxidized 2,3-dialdehyde cellulose; 3: branched PEI (MW 750K and 25K); 4: amino-polysaccharide copolymer "CelloPhos" (PEI MW 750K, DAC:PEI=1:20); FIG. 5B, 5: cellulose; 6: selectively oxidized 2,3-dialdehyde cellulose; 7: branched PLA (MW 58K); 8: amino-polysaccharide copolymer "CelloPhos" (PLA MW 58K, DAC:PLA=1:20); FIG. 5C, 9: amino-polysaccharide copolymer "CelloPhos" (PEI MW 25K, DAC:PEI=1:10); 10: amino-polysaccharide copolymer "CelloPhos" (PEI MW 750K, DAC:PEI=1:20); 11: amino-polysaccharide copolymer "CelloPhos" (PLA MW 58K, DAC:PLA=1:20).

It is seen from FIG. 5 that, the FT-IR spectra of amino-polysaccharide copolymer "CelloPhos" are obviously different from the FT-IR spectra of the reactants. The amino-polysaccharide copolymer "CelloPhos" obtained by embodiments of the present invention has unique FT-IR absorption spectrum.

Example 15 Animal Tests on Reducing Uric Acid

"CELLOPHOS" is the name of the drug comprising amino-polysaccharide copolymers obtained by embodiments of the present invention as active ingredients. In the present example, "CELLOPHOS" comprises 100% amino-polysaccharide copolymers as active ingredients.

Rodent 5008 Fomulab (LabDiet, Louis, Mo.) is used as standard food. "CELLOPHOS" (CelloPhos (PEI MW 750K, DAC:PEI=1:20)) is added into standard food to a proportion of 1 wt % to serve as experimental food. Cellulose is also added into standard foods at a weight ratio of 1% as negative control foods. Female and male rats (Sprague, Dawley) were fed with standard food for 14 days. Plasma uric acid was measured as baseline on day fourteenth by sampling blood samples. The standard food was then replaced with an experimental food and a negative control food. Blood samples were taken again on the twenty-fourth day after food replacement, and plasma uric acid was measured. The experimental results are listed in Table 1. The results in Table 1 show that "CELLOPHOS" significantly reduced the concentration of uric acid in rat plasma.

TABLE 1

"CELLOPHOS" reduces the concentration of uric acid

| | Food types | | | |
|---|---|---|---|---|
| | negative control foods (contain 1% Cellulose weight/weight) | | Experimental foods (contain 1% "CELLOPHOS" weight/weight) | |
| | Gender of animals | | | |
| | Male | Female | Male | Female |
| concentration of uric acid in plasma (mg/ml) | 2.13 ± 0.05 | 2.10 ± 0.15 | 1.60 ± 0.10 | 1.4 ± 0.08 |
| concentration of uric acid in plasma (mg/ml) | 2.12 ± 0.08 | | 1.50 ± 0.07 | |
| Proportion of plasma uric acid in the experimental food group to the negative control food group | 100 ± 3% | | 71 ± 2.9% | |

Example 16 Side Effects

Figure 6:
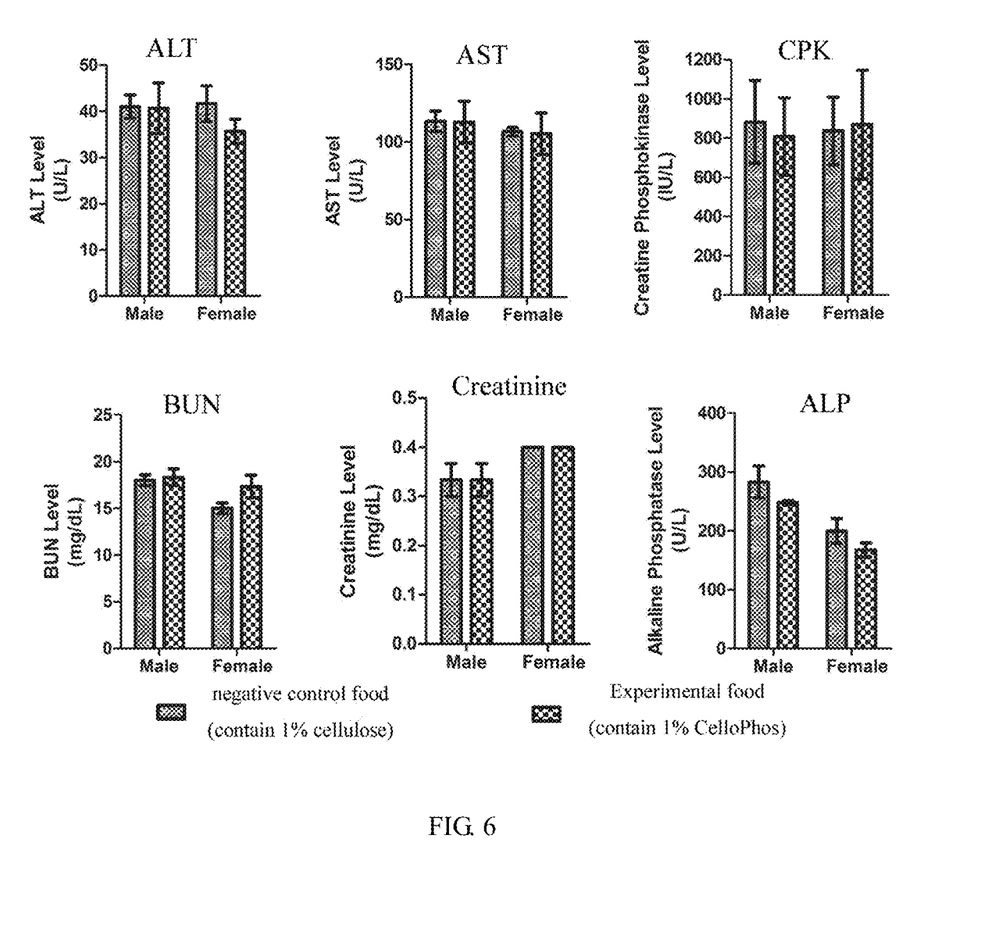
FIG. 6 is a blood biochemical test result of rats three weeks after oral administration of amino-polysaccharide copolymer provided by an embodiment of the present invention.
Figure 7:
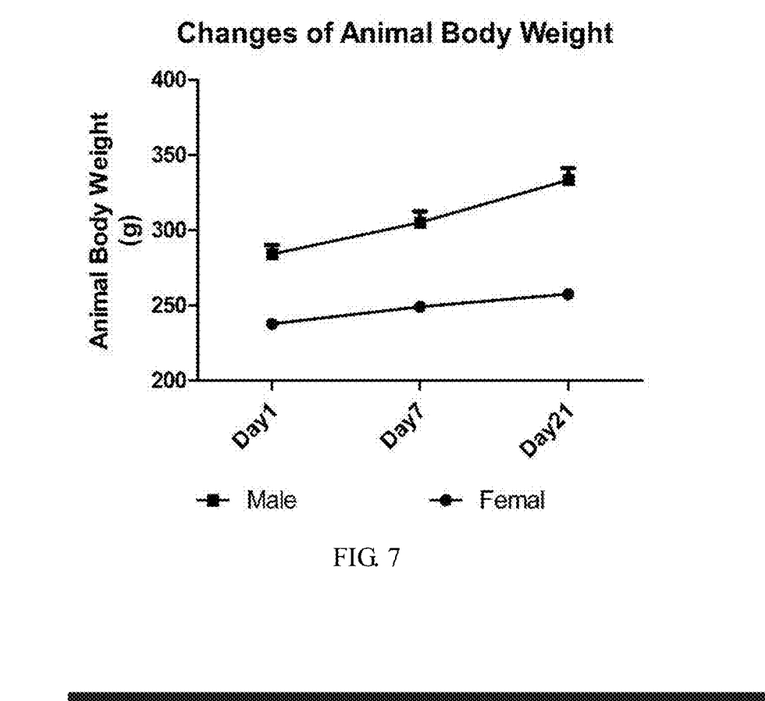
FIG. 7 is a change in body weight of rats during a test of orally administrated amino-polysaccharide copolymers provided by an embodiment of the present invention.
Figure 8:
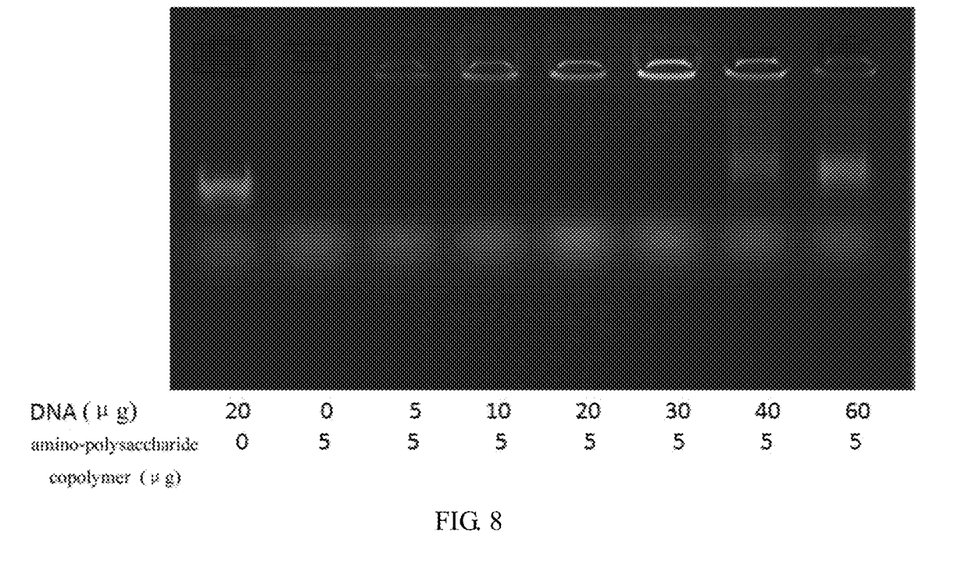
FIG. 8 DNA agarose gel electrophoretic mobility shift assay shows amino-polysaccharide polymers affects the mobility shift assay of deoxyribonucleic acid (DNA) through binding with DNA and blocking displacement of DNA in agar gel electrophoresis experiments.

FIG. 6 shows the blood biochemical test results of rats after taking the amino-polysaccharide copolymer provided by embodiments of the present invention for three weeks. It can be seen from the figure that the amino-polysaccharide copolymer provided by embodiments of the present invention has no obvious influence on the levels of various enzymes in the blood of the rats. It is thus proved that the amino-polysaccharide copolymer provided by embodiments of the present invention is safe and non-toxic. FIG. 7 shows the changes in animal weight during the test. It is seen from the figure, all the animals gained weight throughout the experiment. This data indirectly indicates that taking 1 wt % the amino-polysaccharide copolymer provided by embodiments of the present invention by oral administration does not have any noticeable side effects on the gastrointestinal tract of the tested animals.

Example 17 In Vitro Electrophoresis Shift Experiments on Deoxyribonucleic Acid (DNA) Binding Agar Gel FIG. 7 shows the electrophoresis of DNA, the amino-polysaccharide copolymer, and a mixture of DNA and the amino-polysaccharide copolymer through 0.8% agar gel. The experimental results are shown through UV imaging after ethidium bromide staining.

It is seen from the results of FIG. 7 that the amino-polysaccharide copolymer can combine with DNA in vitro. After combining with the amino-polysaccharide copolymers, After combining with the amino-polysaccharide copolymers, DNA can not shift in the agar gel electrophoresis experiment under the electric field, but stay in the sample groove until saturation of the combining of the amino-polysaccharide copolymers and DNA is reached. The experimental results showed that: 1. 1 gram of amino-polysaccharide copolymer can bind about 6-8 grams nucleic acid until saturation; 2. the amino-polysaccharide copolymers provided by embodiments of the present invention forms a stable combination with DNA, so that the DNA can not be moved under the electrophoresis experiment condition.

What are described above is related to the illustrative embodiments of the disclosure only and not limitative to the scope of the disclosure; the scopes of the disclosure are defined by the accompanying claims.

The present application claims the priority of the U.S. Application No. 62/136,220 filed on Mar. 20, 2015, which is incorporated herein by reference as part of the disclosure of the present application.

What is claimed is:

1. A pharmaceutical composition for treatments of hyperuricemia, the pharmaceutical composition comprises an amino-polysaccharide copolymer and a pharmaceutically acceptable salt thereof as an active ingredient, the amino-polysaccharide copolymer is a copolymerization product of the following two parts:
   a selectively oxidized polysaccharide having a 2,3-dialdehyde moiety, and an amino polymer which provides an amino functionality;
   the amino polymer cross linking the selectively oxidized polysaccharide having a 2,3-dialdehyde moiety to form a net-like structure and finally to provide a hydrogel having an amino functionality or a particulate amino-polysaccharide copolymer, amino functionalities of the hydrogel having an amino functionality or the particulate amino-polysaccharide copolymer can be protonated to form a cationic copolymer having three dimensional network structure and protonation sites, a nitrogen content of the cationic copolymer or the amino-polysaccharide copolymer is at least 12.3% weight percent, or at least 15% weight percent, or at least 22% weight percent, or at least 40% weight percent, the cationic copolymer and the amino-polysaccharide copolymer are both insoluble in water,
   wherein in the selectively oxidized polysaccharide having a 2,3-dialdehyde moiety, a ratio of an amount of oxidized glucose units to the total amount of glucose units is at least 50%, at least 70%, or at least 80%.

2. The pharmaceutical composition according to claim 1, wherein a nitrogen content of the amino polymer which provides an amino functionality is at least 24.5% weight percent, or at least 30% weight percent, or at least 44% weight percent, or at least 80% weight percent.

3. The pharmaceutical composition according to claim 1, wherein a molecular weight of the amino polymer which provides an amino functionality is from about 15,000 to about 900,000.

4. The pharmaceutical composition according to claim 1, wherein the selectively oxidized polysaccharide having a 2,3-dialdehyde moiety is one or more selected from the group consisting of selectively oxidized cellulose, selectively oxidized amylopectin, and selectively oxidized chitosan.

5. The pharmaceutical composition according to claim 1, wherein the selectively oxidized polysaccharide having a 2,3-dialdehyde moiety has at least one of a β-1,4-glycosidic bond or a β-1,6-glycosidic bond.

6. The pharmaceutical composition according to claim 5, wherein the selectively oxidized polysaccharide having a 2,3-dialdehyde moiety has a β-1,4-glycosidic bond and does not have a β-1,6-glycosidic bond.

7. The pharmaceutical composition according to claim 1, wherein the amino polymer which provides an amino functionality is one or more selected from the group consisting of polyethyleneimine (PEI), poly(allylamine), polypropyleneimine (PPI), and polypropylenimine tetramine.

8. The pharmaceutical composition according to claim 1, wherein the amino polymer which provides an amino functionality has a branched structure or a dendritic structure.

9. The pharmaceutical composition according to claim 1, wherein a size of the hydrogel having an amino functionality or the particulate amino-polysaccharide copolymer or the cationic copolymer is from 30 μm to 10 mm, or from 100 μm to 10 mm, or from 300 μm to 5 mm.

10. The pharmaceutical composition according to claim 1, wherein the hydrogel having an amino functionality or the particulate amino-polysaccharide copolymer or the cationic copolymer has pores with diameters less than 50 μm, or has pores with diameters from 100 nm to 50 μm, or has pores with diameters from 200 nm to 40 μm, or has pores with diameters from 300 nm to 30 μm, or has pores with diameters from 400 nm to 20 μm, or has pores with diameters from 500 nm to 10 μm, or has pores with diameters from 800 nm to 5 μm.

11. A method for reducing serum uric acid comprising administering a pharmaceutical composition comprising an amino-polysaccharide copolymer and a pharmaceutically acceptable salt thereof as an active ingredient, wherein, the amino-polysaccharide copolymer is a copolymerization product of the following two parts:
a selectively oxidized polysaccharide having a 2,3-dialdehyde moiety, and an amino polymer which provides an amino functionality;
the amino polymer cross linking the selectively oxidized polysaccharide having a 2,3-dialdehyde moiety to form a net-like structure and finally to provide a hydrogel having an amino functionality or a particulate amino-polysaccharide copolymer, amino functionalities of the hydrogel having an amino functionality or the particulate amino-polysaccharide copolymer can be protonated to form a cationic copolymer having three dimensional network structure and protonation sites, a nitrogen content of the cationic copolymer or the amino-polysaccharide copolymer is at least 12.3% weight percent, or at least 15% weight percent, or at least 22% weight percent, or at least 40% weight percent, the cationic copolymer and the amino-polysaccharide copolymer are both insoluble in water;
wherein in the selectively oxidized polysaccharide having a 2,3-dialdehyde moiety, a ratio of an amount of oxidized glucose units to the total amount of glucose units is at least 50%, at least 70%, or at least 80%.

12. The method according to claim 11, wherein a nitrogen content of the amino polymer which provides an amino functionality is at least 24.5% weight percent, or at least 30% weight percent, or at least 44% weight percent, or at least 80% weight percent.

13. The method according to claim 11, wherein a molecular weight of the amino polymer which provides an amino functionality is from about 15,000 to about 900,000.

14. The method according to claim 11, wherein the selectively oxidized polysaccharide having a 2,3-dialdehyde moiety is one or more selected from the group consisting of selectively oxidized cellulose, selectively oxidized amylopectin, and selectively oxidized chitosan.

15. The method according to claim 11, wherein the selectively oxidized polysaccharide having a 2,3-dialdehyde moiety has at least one of a β-1,4-glycosidic bond or a β-1,6-glycosidic bond.

16. The method according to claim 15, wherein the selectively oxidized polysaccharide having a 2,3-dialdehyde moiety has a β-1,4-glycosidic bond and does not have a β-1,6-glycosidic bond.

17. The method according to claim 11, wherein the amino polymer which provides an amino functionality is one or more selected from the group consisting of polyethyleneimine (PEI), poly(allylamine), polypropyleneimine (PPI), and polypropylenimine tetramine.

18. The method according to claim 11, wherein the amino polymer which provides an amino functionality has a branched structure or a dendritic structure.

19. The method according to claim 11, wherein a size of the hydrogel having an amino functionality or the particulate amino-polysaccharide copolymer or the cationic copolymer is from 30 μm to 10 mm, or from 100 μm to 10 mm, or from 300 μm to 5 mm.

20. The method according to claim 11, wherein the hydrogel having an amino functionality or the particulate amino-polysaccharide copolymer or the cationic copolymer has pores with diameters less than 50 μm, or has pores with diameters from 100 nm to 50 μm, or has pores with diameters from 200 nm to 40 μm, or has pores with diameters from 300 nm to 30 μm, or has pores with diameters from 400 nm to 20 μm, or has pores with diameters from 500 nm to 10 μm, or has pores with diameters from 800 nm to 5 μm.

* * * * *